(12) United States Patent
Roos et al.

(10) Patent No.: US 9,735,477 B2
(45) Date of Patent: Aug. 15, 2017

(54) TERMINAL PIN, FEEDTHROUGH OF AN IMPLANTABLE ELECTROMEDICAL DEVICE AND PROCESS FOR MAKING THE SAME

(71) Applicant: BIOTRONIK SE & Co. KG, Berlin (DE)

(72) Inventors: John Roos, Sherwood, OR (US); Frederik Sporon-Fiedler, Corvallis, OR (US)

(73) Assignee: BIOTRONIK SE & Co. KG, Berlin (DE)

(*) Notice: Subject to any disclaimer, the term of this patent is extended or adjusted under 35 U.S.C. 154(b) by 23 days.

(21) Appl. No.: 14/513,372

(22) Filed: Oct. 14, 2014

(65) Prior Publication Data
US 2016/0104947 A1    Apr. 14, 2016

(51) Int. Cl.
| | | |
|---|---|---|
| *A61N 1/362* | (2006.01) | |
| *A61N 1/39* | (2006.01) | |
| *H01R 4/02* | (2006.01) | |
| *A61N 1/375* | (2006.01) | |

(52) U.S. Cl.
CPC .............. *H01R 4/02* (2013.01); *A61N 1/3754* (2013.01)

(58) Field of Classification Search
CPC ...... A61N 1/362; A61N 1/3956; H01R 43/00; H01R 4/02

USPC .......................................................... 174/650
See application file for complete search history.

(56) References Cited

U.S. PATENT DOCUMENTS

| | | | |
|---|---|---|---|
| 5,944,562 A * | 8/1999 | Christensson | A61B 5/0416 439/261 |
| 7,561,917 B2 * | 7/2009 | Wegrzyn, III | A61N 1/3754 385/138 |
| 8,648,255 B2 | 2/2014 | Talamine et al. | |
| 2004/0112513 A1 * | 6/2004 | Cacace | E04C 5/015 156/221 |
| 2005/0007718 A1 * | 1/2005 | Stevenson | A61N 1/3754 361/118 |
| 2011/0232961 A1 | 9/2011 | Teske | |

* cited by examiner

*Primary Examiner* — Jenny L Wagner
*Assistant Examiner* — Michael E Moats, Jr.
(74) *Attorney, Agent, or Firm* — Buchanan Ingersoll & Rooney PC

(57) ABSTRACT

Terminal pin for electrically connecting a carrier of electrical leads or an electronic component by means of a solder connection between the carrier or component and the terminal pin, wherein an end of a pin body is provided with a swaged cap of a material which is harder than the material of the pin body and which has an outer surface which is suitable for making the solder connection, wherein the cap has an inner circumferential edge where the cap is at least locally narrowed to inside of the outer circumference of the pin body, and wherein there is no additional material between the pin body and the cap.

18 Claims, 5 Drawing Sheets

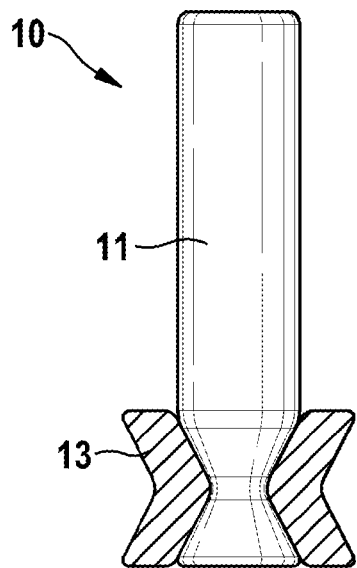
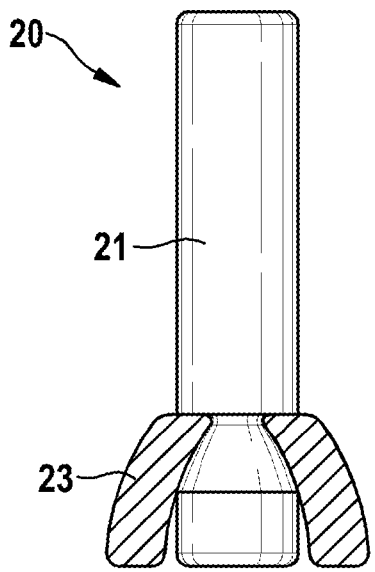
FIG. 1   FIG. 2
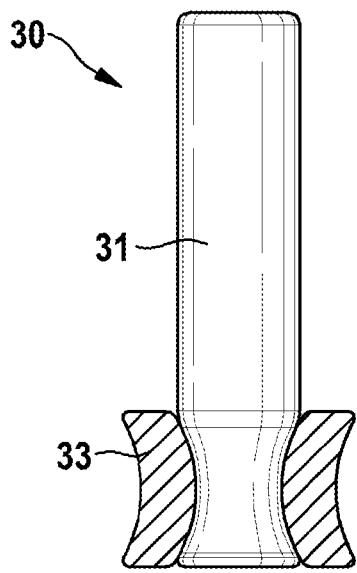
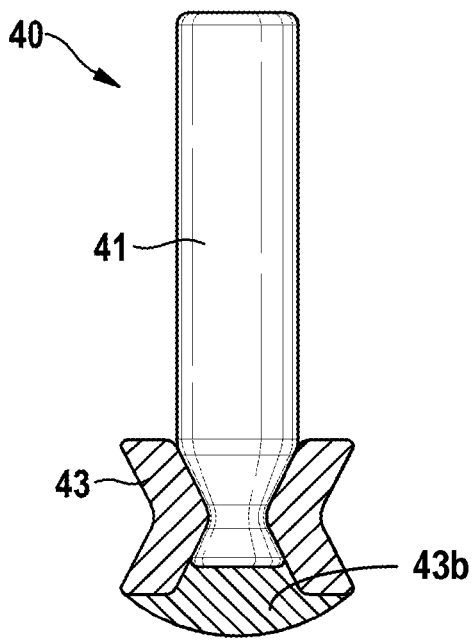
FIG. 3   FIG. 4

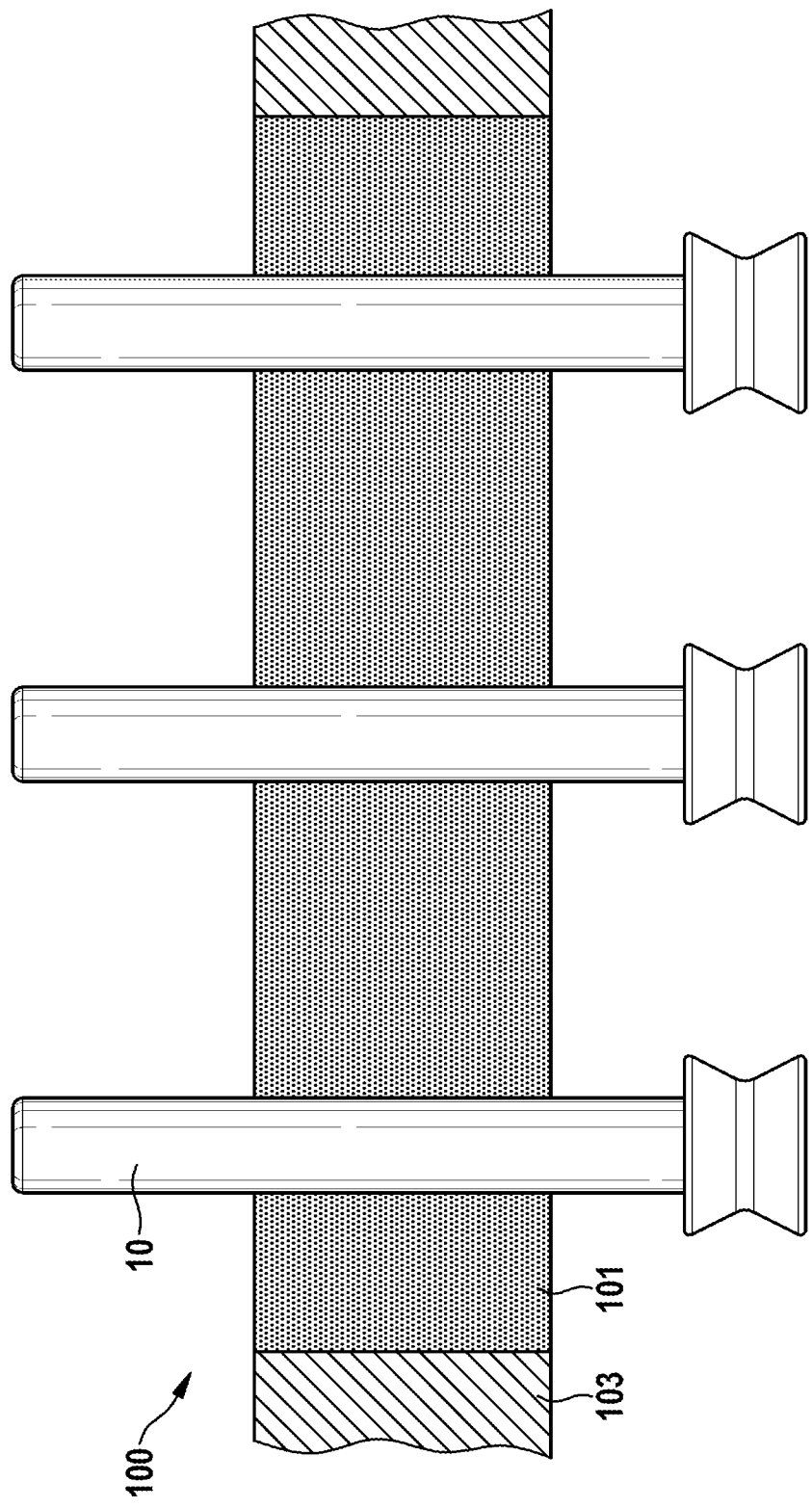

TERMINAL PIN, FEEDTHROUGH OF AN IMPLANTABLE ELECTROMEDICAL DEVICE AND PROCESS FOR MAKING THE SAME

TECHNICAL FIELD

The present invention is related to a terminal pin for electrically connecting a carrier of electrical leads or an electronic component by means of a solder connection between the carrier or component and the terminal pin. Furthermore, the present invention is related to a feedthrough of an implantable electromedical device, in particular, a heart pacemaker or cardioverter. Moreover, the present invention is related to a process for making such a feedthrough.

BACKGROUND

Most of the practically important implantable electromedical devices are adapted for applying electrical pulses to bodily tissue by means of appropriately positioned electrodes. For implementing this function, in the housing of the device, electronic/electrical functional units are provided for generating the pulses and for suitably controlling the pulse generation, whereas on the outer surface of the device, electrodes or contacts for at least one electrode lead are provided, which lead then has the electrodes for applying the pulses to the tissue arranged in its distal end portion. The electronic/electrical functional units within the device are to be connected to the outer electrodes or lead contacts in an adequate manner, which ensures an absolutely and long-term reliable function even under the specific conditions of the implanted state of the device.

This is solved by so-called feedthroughs, which have been the subject of numerous and largely different developments. In many such feedthroughs, terminal pins are provided, which extend from a printed circuit board or a similar carrier of electrical leads to outside the housing of the functional units. These terminal pins and, more specifically, their electrical and mechanical connection to the carrier, have to satisfy highest standards with regard to their reliability even under the influence of bodily fluids.

Therefore, terminal pins have been developed and used, which consist of a noble metal (e.g., platinum) and which can be connected to the lead carrier in a soft solder process in an easy and reliable way, but which are very costly. Besides such terminal pins, multi-part configurations are available, which comprise a terminal pin body and a soft-solderable supplement (pad) made from different materials.

U.S. Pat. No. 8,648,255 discloses terminal pins that include a refractory metal partially welded to a terminal plug of a dissimilar metal incorporated into feedthrough filter capacitor assemblies. The outer surface of the terminal pins is, in different portions of their longitudinal extension, provided with different coatings, i.e., metallization materials, such as, for example, titanium or similar metals, noble metals such as copper, carbon or combinations thereof, or braze materials like gold or silver. At one of the ends of the terminal pins, a Pd plated cap is bonded to the end surface of the pin by means of a laser spot weld.

In U.S. Publication No. 2011/0232961 of the Applicant, an electrical feedthrough for use in an electromedical implant is disclosed, which feedthrough contains terminal pins each of which has at least one section which can be jointed at a lower energy in the interior of the implant. Such pin section can, more specifically, be formed as a nailhead, which on its end face or in its entirety is wetted by a soft solder layer. The nailhead is implemented as a disc-shaped attachment which is soft soldered on the respective cylindrical pin body. The coating of the nailhead portion is made by dipping the pin end into a PbSn eutectic solder.

The present invention is directed toward overcoming one or more of the above-mentioned problems.

SUMMARY

It is an object of the present invention, to provide an improved terminal pin which can be manufactured in a simple and cost-efficient manner, and which is suitable for making a reliable long-term connection of lead carriers inside a medical implant to the outside of the implant. It is a further object of the present invention, to provide an improved feedthrough of such medical implant, and to provide a simple and cost-efficient process for making such a feedthrough. Under process aspects, it is desirable to provide a surface-mount assembly of the feedthrough, whereas the terminal pins as such should be made from a weldable method.

These objects are, among others, solved by a terminal pin according to claim 1 and by a feedthrough according to claim 8. In its process aspect, at least the object is solved by a process in accordance with claim 10.

It is an aspect of the present invention, to provide an end of a pin body with a swaged cap of a material which is harder than the material of the pin body, without an additional solder or braze material between the pin body and the cap. It is a further aspect of the present invention, to press the cap onto an end of the pin such that the cap has an inner circumferential edge where the cap is at least locally narrowed to inside the outer circumference of the pin body. This can be considered as a crimping or clamping of the cap onto the pin body. It is a further aspect of the present invention, that the cap has at least an outer surface which is soft solderable.

The process for making such pin neither contains a step of coating some portion of the pin body for the cap, respectively, with a solder or braze material, nor does it require any thermal step.

In an embodiment of the present invention, at least the inner wall of the cap is narrowed in its middle portion. More specifically, this embodiment can be implemented such that even the outer wall of the cap is narrowed in its middle portion. Irrespective of the position of the narrowing with respect to the longitudinal extension of the cap, the narrowing can either be local (e.g., in two radially opposite points of the inner wall thereof), or it can be a ring-like or circumferential narrowing).

In a further embodiment, the cap body is made from a relatively hard material, such as, for example, copper or constantan, as compared to a softer pin body material, such as, for example, niobium or a Pt/Ir alloy. On the other hand, soft solderable material, such as, for example, a noble metal or noble metal alloy or ENIG, is comprised in an outer surface layer of the cap, e.g., as a plating.

In a further embodiment, the free end surface of the cap is open and protrudes over the corresponding end of the pin body. In an alternative embodiment, the free end surface of the cap is closed unitary with the material of the cap or is filled with a solder material.

An embodiment of the inventive feedthrough comprises a plurality of terminal pins as specified above, in such arrangement that the terminal pins are arranged or embedded in an insulating body of the feedthrough and electrically insulated against each other, and the ends of the terminal pins provided with the caps protrude from the corresponding surface of the insulating body.

According to process aspects of the present invention, a process for making such feedthrough comprises the following steps:

providing a forming tool which comprises a plurality of cavities each of which is adapted to the cap preform of a terminal pin, inserting a plurality of cap preforms, corresponding to the plurality of pin bodies of the feedthrough, into the cavities of the forming tool, effecting a relative motion between a feedthrough provided with the pin bodies and the forming tool such that those ends of the pin bodies, which are to be provided with the caps, plunge into the cavities of the forming tool, actuating the forming tool such that the cavities with the cap preforms comprised therein are narrowed and thereby the caps are crimped punctually, in sections or circumferentially around the respective ends of the pin bodies, and opening the forming tool and discharging the feedthrough comprising the terminal pins provided with the caps.

In an embodiment of the present invention, this process comprises an additional step of coating the ends of the terminal pins which are provided with the caps with a solder material.

In a further embodiment of the present inventive process, cap preforms are used which have a pre-formed narrowing in their middle portion at least of their inner wall. In an alternative implementation of the process, the cap preforms comprise a cylindrical inner wall, and a forming tool is being used, the cavities of which have a narrowing in the middle portion of their inner wall. In one form, there is no additional material between the pin body and the cap.

At least in embodiments of the present invention, the novel terminal pin or feedthrough, respectively, and the process of making the same are clearly advantageous over the prior art under one or more of the following aspects:

The pin body can be made from a material which is optimal for welding, whereas one end of the pin is being made optimal for soldering, without requiring expensive tooling and high labor content.

The process is easy to control, and the perpendicularity and concentricity of the solderable end with respect of the pin body can be ensured in a simple manner.

The process can easily be automated, which further reduces the required labor content and labor cost.

No specific material is required for connecting the cap to the pin body, which simplifies logistics and avoids an additional cost factor.

No thermal step is required, which simplifies the manufacturing equipment and reduces the energy consumption thereof.

The terminal pin configuration offers the option to avoid a solder precoating or pre-tinning step.

Further features, aspects, objects, advantages, and possible applications of the present invention will become apparent from a study of the exemplary embodiments and examples described below, in combination with the Figures, and the appended claims.

DESCRIPTION OF THE DRAWINGS

Preferred embodiments and refinements of the terminal pin and the feedthrough are disclosed, which features, details, and advantages will become clear from the following description of an exemplary embodiment on the basis of the appended drawing. In the drawing:

FIG. 1 is a schematic sectional view of a terminal pin according to an embodiment of the present invention, FIG. 2 is a schematic sectional view of a terminal pin according to an embodiment of the present invention, FIG. 3 is a schematic sectional view of a terminal pin according to an embodiment of the present invention, FIG. 4 is a schematic sectional view of a terminal pin according to an embodiment of the present invention, FIG. 8 is a schematic view of a feedthrough according to an embodiment of the present invention.

DETAILED DESCRIPTION

Figure 5:
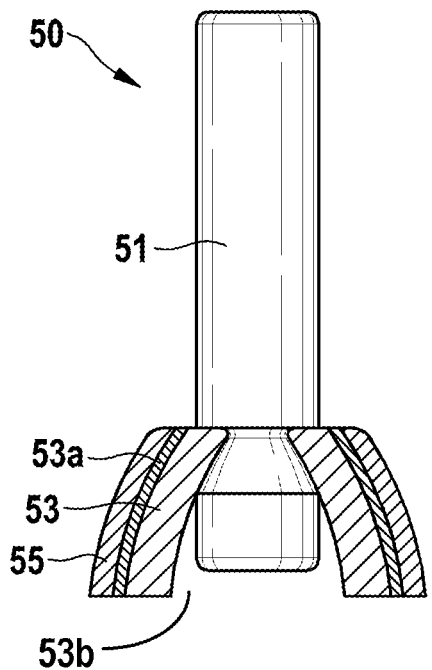
FIG. 5 is a schematic sectional view of a terminal pin according to an embodiment of the present invention.

FIG. 1 shows, in a longitudinal sectional view, a terminal pin 10 which comprises a cylindrical pin body 11 made from a standard terminal pin material, such as, for example, niobium or a Pt/Ir alloy or a similar alloy, and at one end of the pin body 11, a doughnut shaped cap 13 which is swaged onto the pin body. In this embodiment, the cap 13 has a central or middle portion, respectively, which is narrowed with respect to both its ends and which forms a circumferential edge which is inside of the "undisturbed" cylindrical surface of the pin body 11. This is achieved by choosing a harder material for the cap, such as copper or constantan and applying an external pressure radially to the outer wall of the cap, with the pin body inserted into the cap, at certain points or circumferentially in the central portion of the cap. The cap is made soft solderable, by providing an ENIG or noble metal plating 13a on the outer wall thereof.

FIG. 2 shows a terminal pin 20 according to a further embodiment of the present invention, which differs from the terminal pin 10 explained above merely in that the narrowed inner circumferential edge of the solderable cap 23 is provided at the upper end of the cap, rather than in its central portion. Such configuration can be made by applying the above-referenced, radially oriented external pressure not in the central portion but at the upper edge of the cap.

In FIG. 3, a further terminal pin 30 is shown, which is very similar to the pin 10 of FIG. 1, except that the cap 33 thereof does not have a sharp narrowed inner circumferential edge but, rather, a softly impressed central portion.

A further terminal pin 40, as shown in FIG. 4, differs from the terminal pin 30 of FIG. 3 in so far as the lower end of the pin body 41 is not flush with the lower end of the cap 43 but, rather, forms a recess 43b in the cap. This recess can be filled with a solder material 45, e.g., tin or some tin alloy.

FIG. 5 shows a terminal pin 50 which is similar to the terminal pin 20 shown in FIG. 2 but which has a recess 53b within the cap 53, at the corresponding end of the pin body 51. Different from the embodiment shown in FIG. 4, this recess is not filled with a solder material. Rather, the outer wall of the cap 53 is covered with a solderable plating 53a and a solder material 55.

Figure 6:
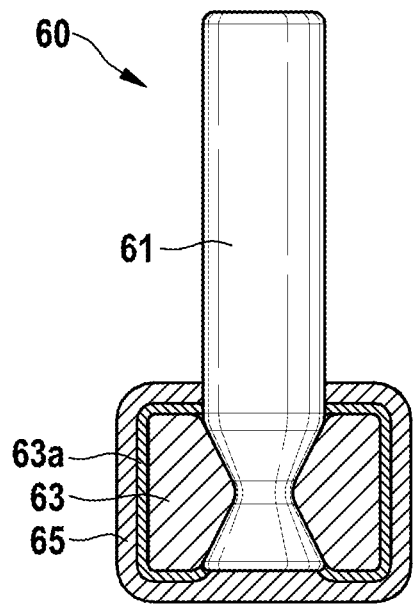
FIG. 6 is a schematic sectional view of a terminal pin according to an embodiment of the present invention.

FIG. 6 shows, at a further embodiment, a terminal pin 60, the cap 63 of which has a cylindrical outer wall, whereas the inner wall thereof is formed similar to the first embodiment shown in FIG. 1, i.e., has a sharply narrowed inner circumferential edge impressed into the softer material of the pin body 61. Such configuration can be made by using a cap which is preformed as shown in the FIG. 6, and which is then circumferentially narrowed in its entirety, in a correspondingly arranged forming tool.

In this embodiment, the entire outer surface of the cap 63 is provided with a solderable plating 63a, and both the entire surface of the cap and the corresponding end face of the pin body 61 have a protective and soft solderable coating 65, e.g., with a soft solder containing, for example, tin or, more specifically an Sn/Pb alloy.

Figure 7:
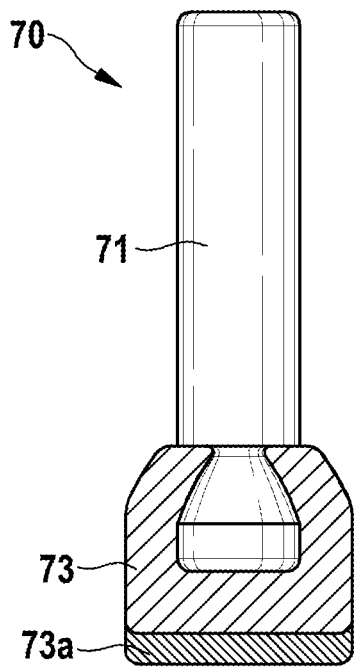
FIG. 7 is a schematic sectional view of a terminal pin according to an embodiment of the present invention.

FIG. 7 shows, as a further embodiment, a terminal pin 70, wherein a pin body 71 rests in a cup-shaped end cap 73, i.e., a cap which has a closed bottom. In this embodiment, only the bottom of the cap 73 is provided with a solderable coating 73a. This specific shape of the cap 73 protects the corresponding end portion of the terminal pin 70 from corrosion to a far extent, without an additional protective coating.

The above-referenced terminal pin configurations can be modified in a manifold manner, regarding the specific shapes of the cap and their position relative to the pin body, as well as regarding the configuration of solderable surface portions of the cap and the optional provision of pre-coated soft solder material thereon. It may even be considered to avoid a specific soft solderable surface layer or plating, respectively, if a cap material is being used which is both harder than an appropriate weldable pin body material and solderable as such.

Figure 9A:
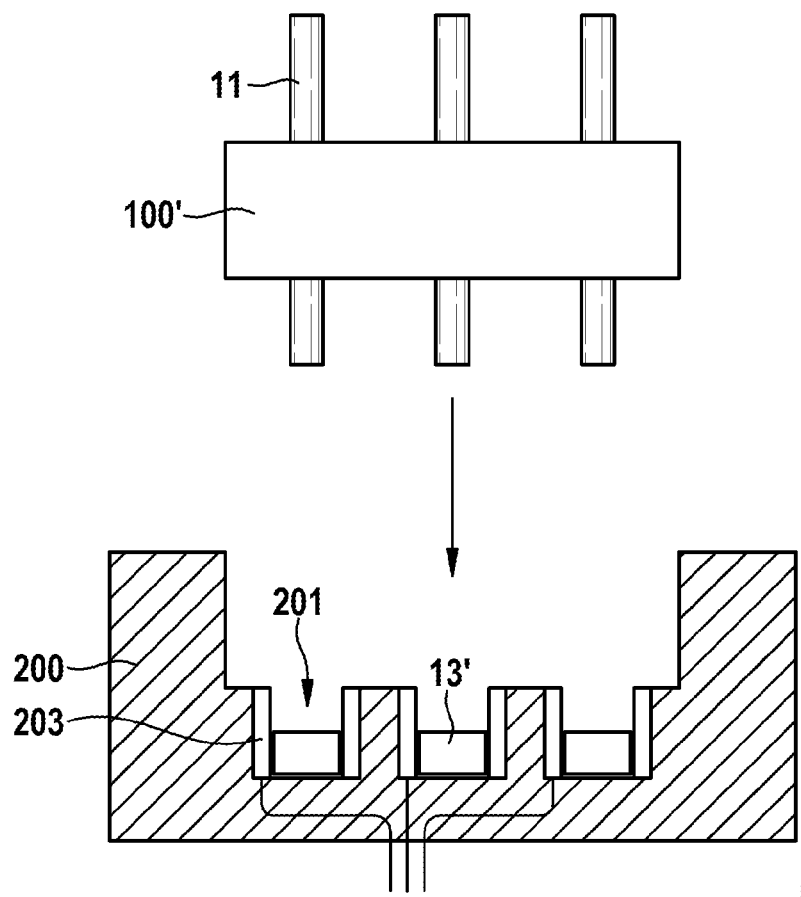
FIGS. 9A to 9D are schematic views of several steps of an embodiment of the process of making such a feedthrough.

FIG. 8 schematically shows a feedthrough 100 of a type which can be used in a heart pacemaker or implantable cardioverter, respectively. The feedthrough 100 comprises plural terminal pins 10 (or any other type of terminal pin, as shown in FIGS. 2-6) extending through an insulator body 101 with some distance to each other, e.g., electrically insulated from each other. A metal flange 103 circumferences the insulator body 101 and serves for mounting (welding) the feedthrough 100 to a housing (not shown) of the heart pacemaker or cardioverter FIG. 9A schematically shows a pre-stage of the feedthrough 100 according to FIG. 8, namely a feedthrough 100' already containing pin bodies 11 but not yet the caps at their respective ends. This incomplete feedthrough 100' is set into a forming tool 200 which comprises a plurality of cavities 201, each of which containing a cap preform 13' and each being surrounded by an actuator element 203 for reducing the lateral extension of the respective cavity. The incomplete feedthrough 100' is set into the forming tool 200 such that each of the pin bodies 11 dives into one of the cap preforms 13'.

Figure 9B:
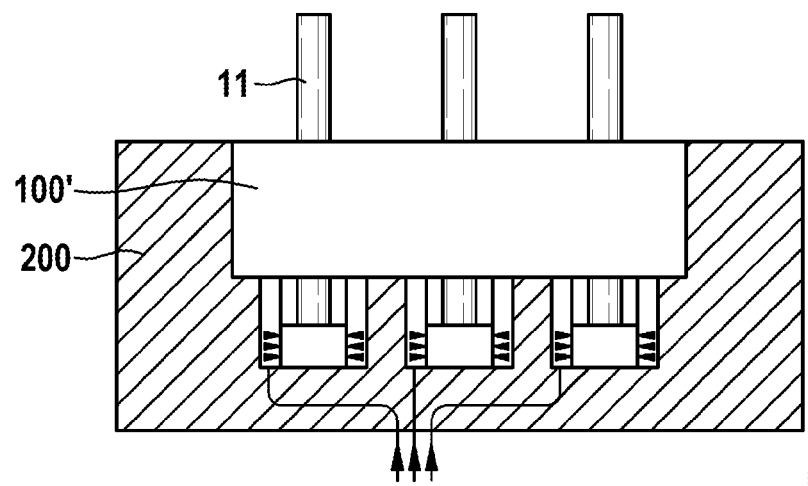

This state is shown in FIG. 9B, and in this state the actuator elements 203 are activated, such as to press the walls of each of the cavities 201 (at least at selected points thereof) radially inwards and to deform the cap preforms 13' to be swaged on the ends of the pin bodies 11 and to assume their final shape as caps 13.

Figure 9C:
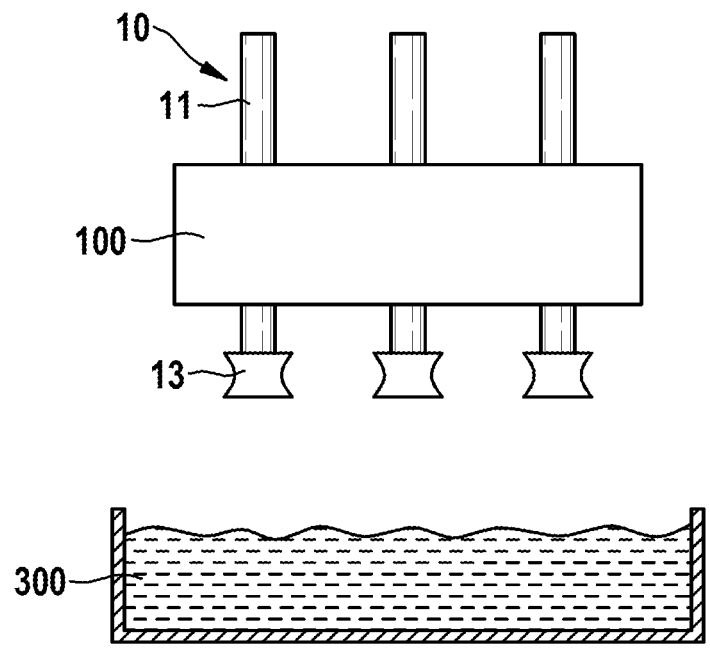
Figure 9D:
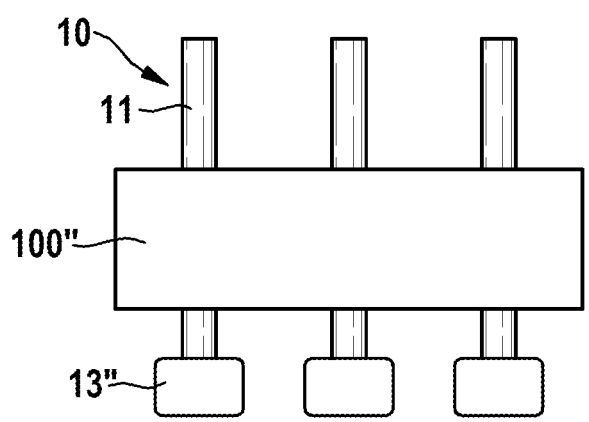

FIG. 9C shows a correspondingly completed feedthrough 100, to be immersed into a solder bath 300 for covering the entire surfaces of the caps 13 with solder, like, for example, a tin alloy; and FIG. 9D shows the feedthrough 100", ready to make solder connections with a PCB or similar device at those ends of the terminal pins 10 where the pre-tinned caps 13" sit.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. A terminal pin for electrically connecting a carrier of electrical leads or an electronic component by means of a solder connection between the carrier or component and the terminal pin, the terminal pin comprising:
    a pin body; and
    a swaged preform cap provided at an end of the pin body, the swaged preform cap of a material which is harder than a material of the pin body and which has an outer surface which is suitable for making the solder connection, wherein the swaged preform cap has an inner circumferential edge where the swaged preform cap is narrowed via a pre-formed narrowing at least locally to inside of the outer circumference of the pin body, and wherein there is no additional material between the pin body and the swaged preform cap,
    wherein an inner wall of the swaged preform cap is narrowed in its middle portion,
    wherein an outer wall of the swaged preform cap is cylindrical,
    wherein an entire outer surface of the swaged preform cap is provided with a solderable plating, and
    wherein both the entire outer surface of the swaged preform cap and a corresponding end face of the pin body have a protective and soft solderable coating.

2. The terminal pin of claim 1, wherein the inner wall of the swaged preform cap is narrowed circumferentially in its middle portion.

3. The terminal pin of claim 1, wherein the swaged preform cap comprises a cap body from a hard material comprising copper or constantan.

4. The terminal pin of claim 1, wherein an outer surface layer of the swaged preform cap comprises a solderable material comprising a noble metal or ENIG.

5. The terminal pin of claim 1, wherein the free end surface of the swaged preform cap is open and protrudes over the corresponding end of the pin body.

6. The terminal pin of one of claim 1, wherein the free end surface of the swaged preform cap is closed unitary with the material of the cap or is filled with a solder material.

7. A feedthrough of an implantable electromedical device, such as a heart pacemaker or cardioverter, the feedthrough comprising:
    at least one terminal pin according to claim 1.

8. The feedthrough of claim 7, further comprising a plurality of terminal pins according to claim 1 in such arrangement that the terminal pins are arranged in an insulating body of the feedthrough and electrically insulated against each other, and the ends of the terminal pins provided with the swaged preform caps protrude from the corresponding surface of the insulating body.

9. A process for making a feedthrough of claim 8, comprising the steps of:
    providing a forming tool which comprises a plurality of cavities, each of which is adapted to a cap preform of a terminal pin;
    inserting a plurality of cap preforms, each cap preform having a pre-formed narrowing corresponding to each one of the plurality of pin bodies of the feedthrough, into the cavities of the forming tool;

effecting a relative motion between the feedthrough provided with the pin bodies and the forming tool such that those ends of the pin bodies, which are to be provided with the cap preforms, plunge into the cavities of the forming tool;

actuating the forming tool such that the cavities with the cap preforms comprised therein are narrowed and thereby the cap preforms are crimped punctually, in sections or circumferentially around the respective ends of the pin bodies to generate a plurality of the swaged preform caps; and opening the forming tool and discharging the feedthrough comprising the terminal pins, each provided with the swaged preform cap.

10. The process of claim 9, further comprising the additional step of coating the ends of the terminal pins which are provided with the swaged preform caps with a solder material.

11. The process of claim 9, wherein cap preforms are being used, which comprise a cylindrical inner wall, and wherein a forming tool is being used, the cavities of which have a narrowing in the middle portion of their inner wall.

12. The process of claim 9, wherein the process is carried out at ambient temperature.

13. The terminal pin of claim 1, wherein the inner circumferential edge is narrowed at an upper end of the swaged preform cap.

14. The terminal pin of claim 1, wherein a lower end of the swaged preform cap is flush with, but does not cover, a corresponding end face of the pin body.

15. The terminal pin of claim 1, wherein a lower end of the swaged preform cap extends beyond a corresponding end face of the pin body to form a recess.

16. The terminal pin of claim 15, wherein the recess is filed with solder material.

17. The terminal pin of claim 15, wherein the swaged preform cap further comprises an outer wall covered with solderable plating and a solder material.

18. A terminal pin for electrically connecting a carrier of electrical leads or an electronic component by means of a solder connection between the carrier or component and the terminal pin, the terminal pin comprising:

a pin body; and a swaged preform cap provided at an end of the pin body, the swaged preform cap of a material which is harder than a material of the pin body and which has an outer surface which is suitable for making the solder connection, wherein the swaged preform cap has an inner circumferential edge where the swaged preform cap is narrowed via a pre-formed narrowing at least locally to inside of the outer circumference of the pin body, and wherein there is no additional material between the pin body and the swaged preform cap, wherein the swaged preform cap has a cup shape with a closed bottom and the pin body rests in the cup shape portion of the swaged preform cap; and wherein solderable coating is provided only at a bottom of the swaged preform cap.

* * * * *